(12) United States Patent
Martel et al.

(10) Patent No.: US 7,962,194 B2
(45) Date of Patent: Jun. 14, 2011

(54) METHOD AND SYSTEM FOR PROPELLING AND CONTROLLING DISPLACEMENT OF A MICROROBOT IN A BLOOD VESSEL

(75) Inventors: Sylvain Martel, Newton, MA (US);
Jean-Baptiste Mathieu, Montréal (CA);
L'Hocine Yahia, Pointe-Claire (CA);
Gilles Soulez, Outremont (CA); Gilles Beaudoin, St-Lambert (CA)

(73) Assignees: Polyvalor, Limited Partnership, Montreal (CA); Val-Chum, Limited Partnership, Montreal (CA)

( * ) Notice: Subject to any disclaimer, the term of this patent is extended or adjusted under 35 U.S.C. 154(b) by 875 days.

(21) Appl. No.: 10/417,475

(22) Filed: Apr. 15, 2003

(65) Prior Publication Data
US 2004/0210128 A1 Oct. 21, 2004

(51) Int. Cl.
*A61B 5/05* (2006.01)
(52) U.S. Cl. .......................... 600/411; 600/424
(58) Field of Classification Search .................. 600/411, 600/424; 606/130
See application file for complete search history.

(56) References Cited

U.S. PATENT DOCUMENTS

| | | | | |
|---|---|---|---|---|
| 4,278,077 A | * | 7/1981 | Mizumoto | 600/109 |
| 4,863,715 A | * | 9/1989 | Jacobsen et al. | 424/9.32 |
| 5,125,888 A | * | 6/1992 | Howard et al. | 600/12 |
| 6,127,597 A | * | 10/2000 | Beyar et al. | 606/86 |
| 6,148,823 A | * | 11/2000 | Hastings | 128/897 |
| 6,157,853 A | * | 12/2000 | Blume et al. | 600/426 |
| 6,298,259 B1 | * | 10/2001 | Kucharczyk et al. | 600/411 |
| 6,304,769 B1 | * | 10/2001 | Arenson et al. | 600/424 |
| 6,939,290 B2 | * | 9/2005 | Iddan | 600/109 |
| 2002/0087177 A1 | * | 7/2002 | Wallace et al. | 606/157 |
| 2004/0054279 A1 | * | 3/2004 | Hanley | 600/424 |

OTHER PUBLICATIONS

Rushmer, *Structure and Function of the Cardiovascular System*, W. B. Saunders Company, 1972., pp. 7-8 and 15.
Milnor, *Hemodynamics*, Williams & Wilkins, 1982, p. 16 and p. 141.
Wham et al., *Effects on flow past solid spheres at finite Reynolds number*, Industrial & Engineering Chemistry Research, vol. 35, No. 3., Mar 1996, pp. 864-874.
Morita et al., *A cylindrical shaped micro ultrasonic motor utilizing PZT thin film (1.4 mm in diameter and 5.0 mm long stator transducer)*, Sensors and Actuators, A: Physical: The 10th International Conference on Solid-State Sensors and Actuators Transducers '99, Jun. 7-Jun. 10, 1999, vol. 83, No. 1, May, pp. 225-230, Inst of Physical and Chemical Research (RIKEN), Saitama, Japan.

(Continued)

*Primary Examiner* — Tse Chen
*Assistant Examiner* — Jacqueline Cheng
(74) *Attorney, Agent, or Firm* — J-Tek Law PLLC; Jeffrey D. Tekanic (57) ABSTRACT

A magnetic resonance imager (MRI) controllably propels at least one magnetic field responsive body within a subject. The MRI comprises a bore magnet producing an intense magnetic field sufficient to magnetically saturate the magnetic field responsive body. A magnetic field gradient generator is configured to apply variable magnetic gradients to at least a portion of the subject containing the magnetically-saturated body. A controller instructs the magnetic field gradient generator to acquire image data of the magnetically-saturated body within the subject and to apply a calculated magnetic gradient that will propel the magnetically-saturated body towards a target location in the subject. A tracking unit of the MRI provides position feedback information of the magnetically-saturated body within the subject.

26 Claims, 5 Drawing Sheets

OTHER PUBLICATIONS

Morita et al., *A cylindrical micro-ultrasonic motor (stator transducer size: 1.4 mm in diameter and 5.0 mm long)* Ultrasonics, vol. 38, No. 1-8, Mar. 2000, pp. 33-36, Inst of Physical and Chemical Research (RIKEN), Saitama, Japan.

Grady et al., *Experimental study of the magnetic stereotaxis system for catheter manipulation within the brain*, J Neurosurg, vol. 93, pp. 282-288, Aug. 2000.

Grady et al., *Magnetic stereotaxis: a technique to deliver stereotactic hyperthermia Neurosurgery*, vol. 27, pp. 1010-1015; discussion 1015-6, Dec. 8, 1990.

McNeil, et al., Characteristics of an improved magnetic-implant guidance system, *IEEE Trans Biomed Eng*, vol. 42, pp. 802-808, Aug. 1995.

McNeil et al., Functional design features and initial performance characteristics of a magnetic-implant guidance system for stereotactic neurosurgery, *IEEE Trans Biomed Eng*, vol. 42, pp. 793-801, Aug. 1995.

Ishiyama et al., *Magnetic micromachines for medical applications*, Journal of Magnetism and Magnetic Materials, vol. 242-245, No. 1, April, pp. 41-46, 2002. Res. Inst. of Elec. Communication, Tohoku University, Aoba Sendai 980-8577, Japan.

Sato et al., The Operation of a Magnetic Micromachine for Hyperthermia and its ExothermicCcharacteristic, *2002 International Magnetics Conference (Intermag 2002)*, Apr. 28-May 2, 2002, pp. 3362-3364. [Abstract].

Sendoh et al., Direction and individual control of magnetic micromachine, *2002 International Magnetics Conference (Intermag 2002)*, Apr. 28-May 2, 2002, vol. 38, pp. 3356-3358.

Sendoh et al., Fabrication of magnetic micro-machine for local hyperthermia, *2002 IEEE International Magnetics Conference-2002 IEEE Intermag*, Apr. 28-May 2, 2002, vol. 38, pp. 3359-3361.

Brown, *Principes de Ferromagétisme*, Monographies Dunod, 1970, pp. 14-25.

White, *Fluid Mechanics*, fourth edition, McGraw and Hill, 1999, pp. 451-460.

Lacroux, *Les Aimants Permanents*, Paris: Technique et Documentation, 1989, pp. 125-126.

Mathieu et al., Preliminary studies for using magnetic resonance imaging systems as a mean of propulsion for microrobots in blood vessels and evaluation of ferromagnetic artifacts, Canadian Congress on Electric and Computer Engineering, (CCECE), Montreal, Canada, 2003, pp. 1-5.

Chen, *Magnetism and Metallurgy of Soft Magnetic Materials*, North Holland, 1977, pp. 256-267.

Henderick et al., *MRI: Principles and Artifacts*, Raven Press, 1993.

Jiles, *Magnetism and Magnetic Materials*, Chapman and Hall, 1990.

Kasler, *Comprendre l'IRM: Manuel d'auto apprentissage*, collection d'imagerie radiologique, $3^{rd}$ Edition, 2000.

Kasler, *Principes de l'IRM: Manuel d'auto apprentissage*, coleection d'imagerie radiologique, Masson, 1994.

Wham et al., *Wall Effects on Flow Past Fluid Spheres at Finite Reynolds number: Wake structure and Drag Correlations*, Chemical Engineering Science, vol. 52, No. 19, pp. 3345-3367.

Office Action dated Nov. 2, 2010 from counterpart Canadian patent application No. 2,425,795.

\* cited by examiner

METHOD AND SYSTEM FOR PROPELLING AND CONTROLLING DISPLACEMENT OF A MICROROBOT IN A BLOOD VESSEL

FIELD OF THE INVENTION

The present invention relates to a method and system for propelling and controlling displacement of a microrobot in a blood vessel. Herein, the term "microrobot" is also intended to include devices and structures with dimensions in the micrometer and/or sub-micrometer ranges.

BACKGROUND OF THE INVENTION

Medical applications of microrobots driven inside blood vessels are numerous. Amongst these applications are Minimally Invasive Surgeries (MIS) like angioplasties, and highly localized drug deliveries for chemotherapy or biopsies. The smaller these microrobots are, the wider the operating range becomes through access to the finest blood vessels such as capillaries.

Because of its larger diameter, the arterial system of the human body is being considered as the initial target location where a microrobot can be implanted. With further miniaturization and more precise positioning techniques, smaller regions such as capillaries could also be considered.

The force for propelling and controlling displacement of the microrobot must be stronger than the drag force on this microrobot for motion to take place and to enable control of the displacement of the microrobot in the blood vessels. In order to determine the level of the force required for propelling and controlling displacement of the microrobot, the following parameters must be taken into consideration:

The dimensions of the blood vessels in human beings typically range from 25 mm in diameter (aorta) to approximately 8 μm (capillaries) [R. F. Rushmer, *Structure and Function of the Cardiovascular System*, W. B. Saunders Company, 1972].

The blood flow in the arterial system is pulsatile and much faster at the exit of the heart (ascending aorta: maximal systolic velocity is 1120 mm/s) [W. R. Milnor, *Hemodynamics*, Williams & Wilkins, 1982]. When an artery or vein bifurcates, the cross-sectional area of its branches exceeds that of the parent vessel. Therefore, the blood velocity decreases away from the heart in a similar fashion when water in a rushing stream slows down when entering a broad pool [R. F. Rushmer, *Structure and Function of the Cardiovascular System*, W. B. Saunders Company, 1972].

And, as described in [Wham, R. M., Basaran, O. A., and Byers, C. H., *Wall effects on flow past solid spheres at finite Reynolds number*, Industrial & Engineering Chemistry Research, Vol. 35, No. 3. March, pp. 864-874, 1996. 0888-5885. Oak Ridge Natl Lab, TN, USA], the drag force of a rigid sphere in a rigid cylindrical tube is a function of the density of the fluid ($\rho$), the velocity of the sphere relative to the velocity of the fluid (V), the frontal area (A), the drag coefficient of the sphere ($C_D$), the Reynolds number (Re), and the ratio of the diameter of the sphere to the diameter ($\lambda$) of the cylindrical tube.

The use of micromotors for propelling a microrobot in blood vessels presents the following drawbacks. Micromotors require precise and complex assemblies of several moving parts having increased probability of failure and being difficult to miniaturize and fabricate [Morita, T., Kurosawa, M. K., and Higuchi, T., *Cylindrical shaped micro ultrasonic motor utilizing PZT thin film* (1.4 mm in diameter and 5.0 mm long stator transducer), Sensors and Actuators, A: Physical: The 10th International Conference on Solid-State Sensors and Actuators TRANSDUCERS '99, Jun. 7-Jun. 10, 1999, Vol. 83, No. 1. May, pp. 225-230, 2000. 0924-4247. Inst of Physical and Chemical Research (RIKEN), Saitama, Jpn]. Furthermore, micromotors need to carry along either an energy source or an energy conversion device (battery or induction coil for example), a device to convert the motor torque into motion force (propeller, flagella . . . ) and a device for controlling the direction of the driving force (flaps or MEMS nozzles). The smallest ultrasonic micromotors existing have a 1.4 mm diameter and are 5.0 mm long [Morita, T., Kurosawa, M. K., and Higuchi, T., *Cylindrical micro-ultrasonic motor* (stator transducer size: 1.4 mm in diameter and 5.0 mm long) Ultrasonics, Vol. 38, No. 1-8. March, pp. 33-36, 2000. 0041-624X. Inst of Physical and Chemical Research (RIKEN), Saitama, Jpn], and the propulsion group alone is already too big for vascular applications.

Magnetic propulsion for minimally invasive surgery researches has been implemented at University of Virginia [Grady, M. S., Howard, M. A. 3rd, Dacey, R. G. Jr, Blume, W., Lawson, M., Werp, P., and Ritter, R. C., *Experimental study of the magnetic stereotaxis system for catheter manipulation within the brain*, J Neurosurg, Vol. 93, pp. 282-8, August, 2000; 2] [Grady, M. S., Howard, M. A. 3rd, Broaddus, W. C., Molloy, J. A., Ritter, R. C., Quate, E. G., and Gillies, G. T., *Magnetic stereotaxis: a technique to deliver stereotactic hyperthermia Neurosurgery*, Vol. 27, pp. 1010-5; discussion 1015-6, December 1990.8] [McNeil, R. G., Ritter, R. C., Wang, B., Lawson, M. A., Gillies, G. T., Wika, K. G., Quate, E. G., Howard, M. A. 3rd, and Grady, M. S., *Characteristics of an improved magnetic-implant guidance system*, IEEE Trans Biomed Eng, Vol. 42, pp. 802-8, August, 1995] [McNeil, R. G., Ritter, R. C., Wang, B., Lawson, M. A., Gillies, G. T., Wika, K. G., Quate, E. G., Howard, M. A. 3rd, and Grady, M. S., *Functional design features and initial performance characteristics of a magnetic-implant guidance system for stereotactic neurosurgery*, IEEE Trans Biomed Eng, Vol. 42, pp. 793-801, August, 1995] and at Tohoku University [Ishiyama, K., Sendoh, M., and Arai, K. I., Magnetic micromachines for medical applications, *Journal of Magnetism and Magnetic Materials*, Vol. 242-245, No. 1. April, pp. 41-46, 2002. 0304-8853. Res. Inst. of Elec. Communication, Tohoku University, Aoba Sendai 980-8577, Japan] [Sato, F., Jojo, M., Matsuki, H., Sato, T., Sendoh, M., Ishiyama, K., and Arai, K. I., *The operation of a magnetic micromachine for hyperthermia and its exothermic characteristic*, 2002 International Magnetics Conference (Intermag 2002), Apr. 28-May 2, 2002, pp. 3362-3364, 2002] [Sendoh, M., Ishiyama, K., and Arai, K. I., *Direction and individual control of magnetic micromachine*, 2002 International Magnetics Conference (*Intermag* 2002), Apr. 28-May 2, 2002, pp. 3356-3358, 2002] [Sendoh, M., Ishiyama, K., Arai, K. I., Jojo, M., Sato, F., and Matsuki, H., *Fabrication of magnetic micro-machine for local hyperthermia*, 2002 IEEE International Magnetics Conference-2002 IEEE INTERMAG, Apr. 28-May 2, 2002, pp. FU11, 2002].

The concept studied at University of Virginia is the following: moving a ferromagnetic thermoseed (Video Tumor Fighter VTF) through brain tissue to reach a brain tumor. Once the tumor is penetrated, the thermoseed is heated via eddy current with RF excitation and is moved to scan and destroy the whole tumorous volume. The propulsion is made by applying magnetic field gradients (hence a magnetic force) generated by a Magnetic Stereotaxis System (MSS) which is a homemade device involving six supraconducting coils and a fluoroscopic imaging system. The VTF needs a 5 to 7 T/m magnetic field gradient in order to be able to move straight through thick brain tissue.

The researches from Tohoku University involve a magnet embedded inside a screw shaped body (between 1 and 2 mm in diameter and 8 to 15 mm in length). When applying a rotating magnetic field, the magnet and thus the screw tend to rotate and the system digs its path through tissues. The velocity of the screw shaped system is a function of the magnetic torque, rotational velocity of the field and pitch of the screw.

SUMMARY OF THE INVENTION

According to the present invention, there is provided a method of propelling and controlling displacement of a microrobot through a patient's blood vessel, comprising forming the microrobot with a body containing field-of-force responsive material wherein, in response to a field of force, the material undergoes a force in the direction of a gradient of the field of force, positioning the microrobot in a blood vessel for displacement through the blood vessel, and generating a field of force with a given gradient and applying the field of force to the microrobot in view of propelling the microrobot through the blood vessel in the direction of the gradient of the field of force. Generating the field of force comprises calculating a direction and amplitude of the gradient of the field of force to thereby control displacement of the microrobot through the patient's blood vessel.

The present invention also relates to a microrobot system, comprising:

a microrobot for displacement through a patient's blood vessel, the microrobot being formed with a body containing field-of-force responsive material wherein, in response to a field of force, the material undergoes a force in the direction of a gradient of the field of force; and a generator of a field of force with a given gradient for application to the microrobot in view of propelling the microrobot through the blood vessel in the direction of the gradient of the field of force, wherein the generator comprises a calculator of a direction and amplitude of the gradient of the field of force to thereby control displacement of the microrobot through the patient's blood vessel.

The foregoing and other objects, advantages and features of the present invention will become more apparent upon reading of the following non restrictive description of an illustrative embodiment thereof, given by way of example only with reference to the accompanying drawings.

DETAILED DESCRIPTION OF THE ILLUSTRATIVE EMBODIMENT

An illustrative embodiment of the method and system for propelling and controlling displacement of a microrobot in a blood vessel according to the present invention (hereinafter the illustrative embodiment) will now be described.

As indicated in the foregoing description, medical applications of microrobots driven inside blood vessels are numerous. These include Minimally Invasive Surgeries (MIS) like angioplasties, highly localized drug deliveries for chemotherapy, biopsies, etc. The smaller these microrobots are, the wider the operating range becomes through access to the finest blood vessels such as capillaries. For example, such a microrobot could potentially be released in the vicinity of the treatment area through a catheter. Then, it could be externally guided using a control software and hardware capable of tracking it, computing its trajectory and, finally, determining magnetic field gradients to be applied thereto in order to guide the microrobots along the calculated trajectory. Such a magnetic propulsion concept is extremely promising for miniaturized systems targeted at in vivo applications.

Therefore, in the illustrative embodiment, the microrobot is propelled and its displacement in the blood vessel is controlled by means of magnetic field gradients produced inside this blood vessel. For that purpose, a strong and variable driving magnetic field exerts three-dimensional propulsion forces to a body of magnetic, for example ferromagnetic material mounted to and/or embedded in the microrobot. For example, Magnetic Resonance Imaging (MRI) systems can be used to produce, in a controllable manner, the required three-dimensional magnetic field. An advantage of using an MRI system is that the imaging capabilities of the MRI system may also be possibly used to track the displacement of the microrobot in the blood vessel, thereby providing position feedback information.

Figure 5:
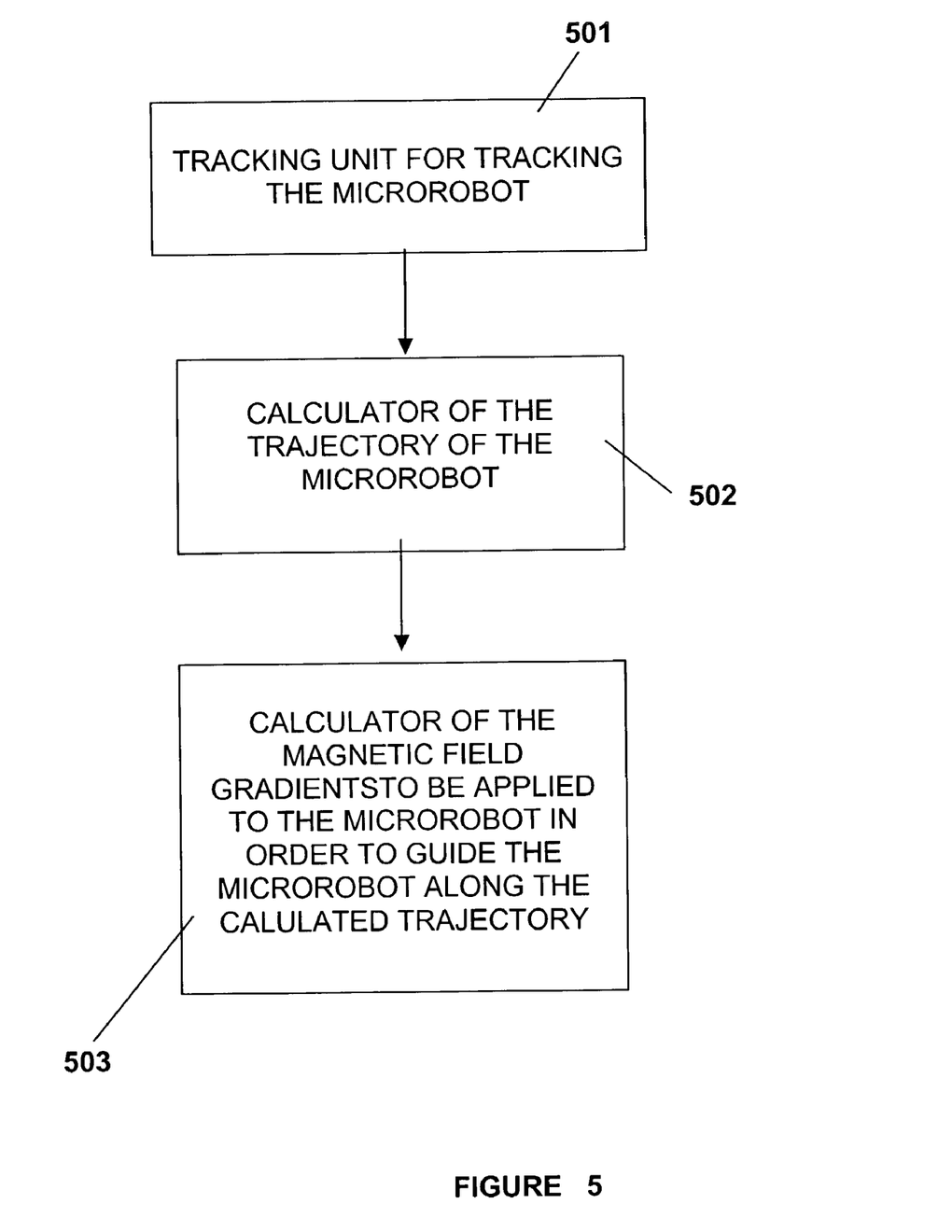
FIG. 5 is a schematic block diagram showing how magnetic field gradients are calculated in the illustrative embodiment of the method and system for propelling and controlling displacement of a microrobot in a blood vessel according to the present invention method.

More specifically, referring to FIG. 5, a tracking unit 501 will track the microrobot to determine the position of this microrobot in the patient's blood vessel (not shown in FIG. 5). Then, a calculator 502 will compute the trajectory of the microrobot taking into consideration the tracked position of the microrobot from unit 501, the configuration of the blood vessel, and the location to be reached by the microrobot. Finally, another calculator 503 will compute the magnetic field gradients to be applied to the microrobot by the MRI system so as to guide this microrobot along the trajectory computed by the calculator 502.

The magnetic force induced by the MRI system must be stronger than the drag force of the blood flow on the microrobot for motion to take place in a blood vessel and to enable control of the displacement.

The torque and the force induced by a MRI system can be estimated [W. F. Brown, *Principes de Ferromagnétisme*, Monographies Dunod, 1970] by the following relations (1) and (2), respectively:

$$\vec{\tau} = \vec{m} \times \vec{B} = \vec{M} * V_{ferro} \times \vec{B} \tag{1}$$

$$\vec{F}_{magnetic} = \vec{M} \cdot V_{ferro} \cdot \nabla \vec{B} \tag{2}$$

In Equations (1) and (2), $\vec{\tau}$ is the magnetic torque (Newton-meter (N-m)), $\vec{F}_{magnetic}$ is the magnetic force (Newton (N)), $\vec{M}$ is the magnetization of the ferromagnetic material (Ampere/meter (A/m)), $V_{ferro}$ is the volume of the body of ferromagnetic material (m³), $\vec{B}$ is the magnetic induction (Tesla (T)) and $\nabla \vec{B}$ is the gradient (spatial variation) of the magnetic induction (Tesla/meter (T/m)).

The blood flow and the diameter of the blood vessels that are visited determine the drag force to which the microrobot is subjected. These parameters are linked to the medical application that has to be performed and determine the quantity of ferromagnetic particles needed, which is related to the size of the microrobot. For example, the drag force of a rigid sphere in a rigid cylindrical tube is a function of the density of the fluid (ρ), the velocity of the sphere relative to the fluid (V), the frontal area (A), the drag coefficient of the sphere ($C_D$), the Reynolds number (Re), and the ratio of the diameter of the sphere to the diameter (λ) of the cylindrical tube.

The quantity of ferromagnetic material needed, which is related to the size of the robot, is determined by the blood flow at the location where the treatment has to be performed within the patient's body. The microrobot can be easily made larger or smaller accordingly to the task of the microrobot and the location of the treatment within the patient's body. This is not the case for internal propulsion systems previously proposed in the literature such as micromotors that involve complex and precise assembly of numerous moving parts with the additional need to carry along their energy source, a major bottleneck in miniaturization. The choice of a Magnetic Resonance Imaging (MRI) system as the means for propelling the microrobot enables to achieve further miniaturization of the microrobot within the patient's body. Two advantages of this approach are that MRI systems not only provide adequate magnetic fields and gradients for propelling the microrobots but they are already available in almost every hospital.

Propulsion and Displacement Control:

Tests were conducted to match (a) the magnetic force induced by a MRI system on a microrobot under the form of a ferromagnetic sphere with (b) the drag force applied to this sphere in a cylindrical conduit where a liquid flows. As a result of these tests, a sphere having a diameter of 3.175 mm diameter and made of 1010/1020 carbon steel was able to withstand a maximum flow of 0.4115 litres/minute in a tube having a diameter of 6.35 mm with a magnetic field gradient of 18 mT/m applied to the sphere by the MRI system.

As blood's density and viscosity are lower than brain tissues, the magnetic field gradients required in the illustrative embodiment to induce a magnetic force sufficiently strong to overcome the drag force of the blood flow on the sphere are weaker than those used by the University of Virginia (see the background of the invention). Since MRI systems provide adequate magnetic field gradients for propulsion and control of the displacement of the microrobots, and since MRI systems are already available in almost every hospital, MRI systems were chosen as the generator of magnetic field gradients for propelling and controlling displacement of the microrobot. A magnetic propulsion system is easy to fabricate and to miniaturize as the propelling force is directly proportional to the volume of ferromagnetic material in the microrobot and as all the required energy comes from the outside. No propeller or micromotor is required, and steering is performed simply by changing the direction of the vector $\nabla \vec{B}$ of the magnetic field gradient. Operation of an MRI system for producing a magnetic field gradient of given direction and amplitude is well known to those of ordinary skill in the art and, accordingly, will not be further described in the present specification.

The smaller the propulsion system is, the smaller the microrobot can be and the wider its operating range becomes. As a matter of fact, a sufficiently small robot could access the capillaries, which could be useful in certain applications. In practice, a microrobot could be released near the treatment area through a catheter. Then, the propulsion and displacement of the microrobot could be controlled through tracking of the microrobot (tracking unit 501 of FIG. 5), calculation of the trajectory of the microrobot (calculator 502) and then determination of the magnetic field gradient to be applied to the microrobot (calculator 503). This magnetic propulsion concept is extremely promising for miniaturized systems targeted at in vivo applications.

Tests

As indicated hereinabove, the aim of the tests was to match the magnetic and drag forces acting on a sphere made of ferromagnetic material. The tests were performed using a ferromagnetic ball having a diameter of 3.175 mm and made of 1010/1020 carbon steel ball, Grade 1000. The saturation induction $\vec{B}_{sat}$ of this alloy is 1.67 T, and is reached within a magnetizing induction of 0.717 T.

Figure 4:
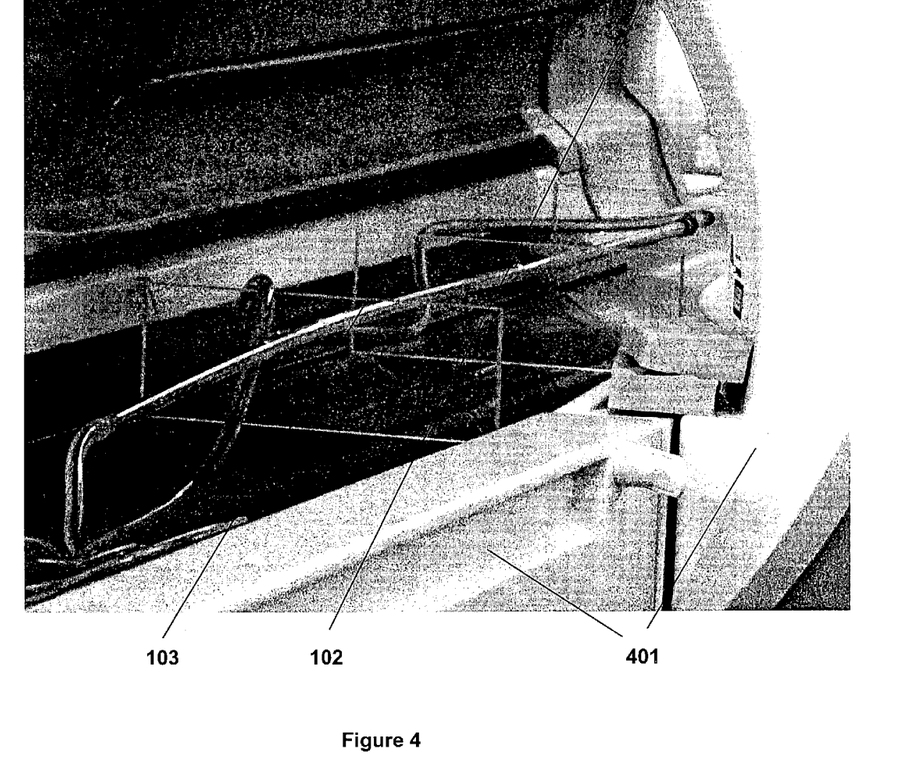
FIG. 4 is a perspective view of the illustrative embodiment of FIG. 1, showing a MRI (Magnetic Resonance Imaging) system.

All tests were performed with a 1.5-T Siemens Magnetom Vision system shown at 401 in FIG. 4 (Hôpital Notre Dame, Montréal, PQ, Canada). This MRI system caused the 1010/1020 carbon steel sphere to be fully magnetized ($\vec{B}_{sat}$).

Figure 1:
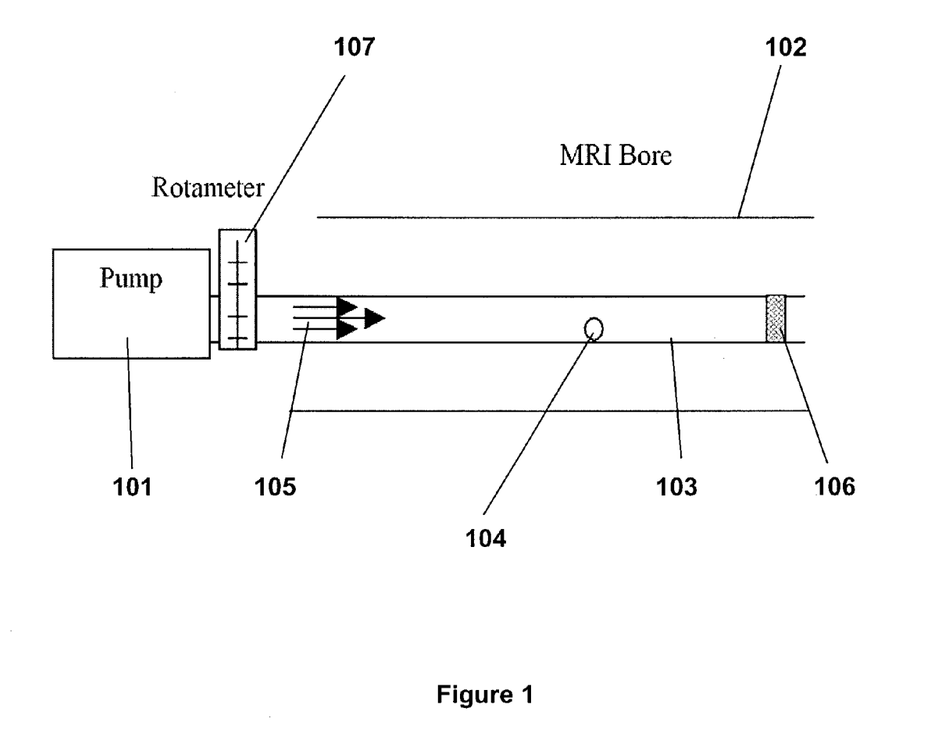
FIG. 1 is a schematic diagram of an illustrative embodiment of a set-up for testing the method and system for propelling and controlling displacement of a microrobot according to the present invention.

As illustrated in FIG. 1, to simulate the flow of blood in an artery, a turbine pump 101 (FIG. 1) placed outside of the MRI chamber produced a flow 105 of liquid (water in this particular example) through a PMMA (poly(methyl methacrylate)) graduated straight tube 103 (FIGS. 1 and 4) having a diameter of 6.35 mm and a length of 1800 mm, located inside the MRI bore 102 (FIGS. 1 and 4). The carbon steel ball or sphere 104 was placed inside the straight tube 103. A net 106 was placed at the outlet of the straight tube 103 to keep the sphere 104 inside of this tube. The length of the straight tube 103 was determined so that the velocity profile of the liquid is fully developed when it reaches the sphere 104. The flow was measured and regulated with a variable-area flowmeter 107 (rotameter) with flow control valve (not shown) interposed between the turbine pump 101 and the inlet of the straight tube 103.

Figure 2:
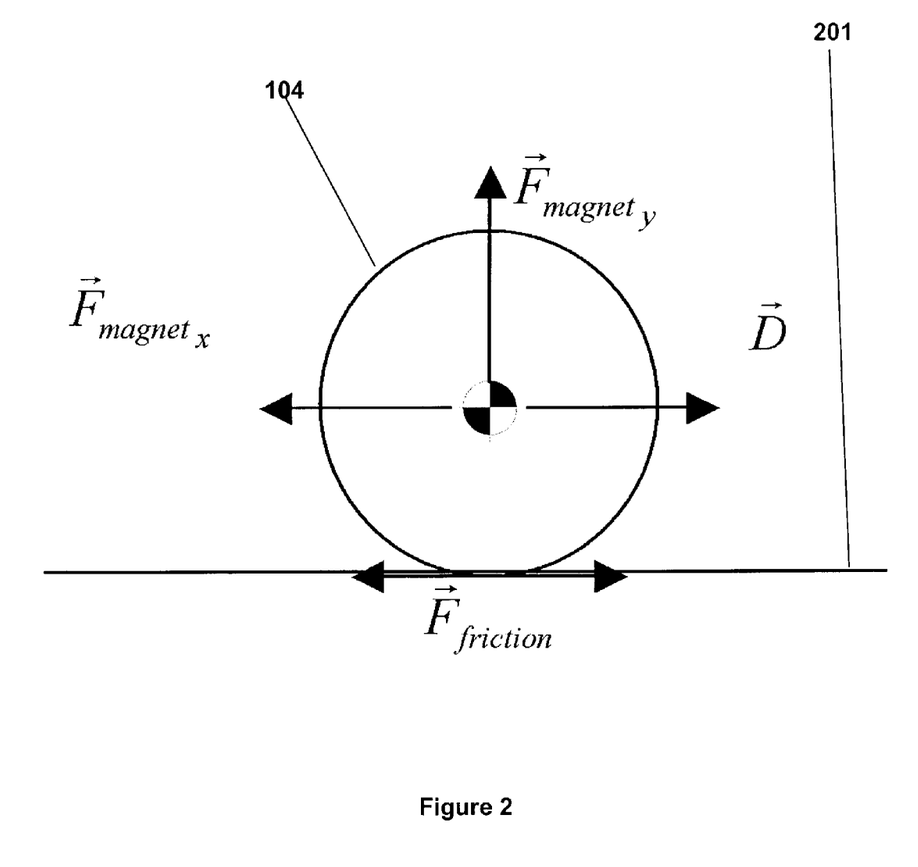
FIG. 2 is a schematic diagram showing magnetic, drag and friction force vectors applied to a sphere of the illustrative embodiment of FIG. 1.

A magnetic field gradient of 18 mT/m was applied along the x ($\vec{F}_{magnet_x}$) and along the y ($\vec{F}_{magnet_y}$) directions of the MRI bore 102 with a cycle of 10 ms on and 2 ms off. The y part $\vec{F}_{magnet_y}$ of the gradient was used to reduce the static and dynamic friction force $\vec{F}_{friction}$ between the sphere 104 and the bottom 201 of the PMMA tube 103. FIG. 2 shows the forces acting on the sphere 104 while at rest.

As the magnetic torque generated by the intense magnetic field (1.5 T) of the MRI system is much stronger than the torques created by all other forces, the sphere 104 cannot roll inside the tube 103. The following calculations show that rolling is impossible. $\vec{B}_{sat}$ can be converted in a saturation magnetization $\vec{M}_{sat}$ of 1330684 A/m. The magnetic moment of the sphere is thus $\vec{m}_{sat} = \vec{M}_{sat} \cdot V_{ferro} = 0.0223$ A·m².

$$\vec{\tau} = \vec{m}_{sat} \times \vec{B} = 0.03 \text{ N.m}$$

-continued $$\vec{F}_{magnetic} R_{sph} = m_{sat} \cdot \vec{\nabla} \vec{B} = 6.37E - 07 \text{ N.m}$$

$$\frac{\vec{\tau}}{\vec{F}_{magnetic} R_{sph}} = 52493.4$$

where $R_{sph}$ is the radius of the sphere.

The ratio between the two above torques clearly indicates that the sphere 104 cannot roll. Friction between the sphere 104 and the walls such as 201 of the tube 103 can be overcome by MRI systems providing gradients such as $\vec{F}_{magnet_y}$ strong enough to levitate the sphere 104. Moreover, this important force of friction can become an asset when anchoring will be needed since a non rolling sphere can be seen like a wheel with brakes on.

Figure 3:
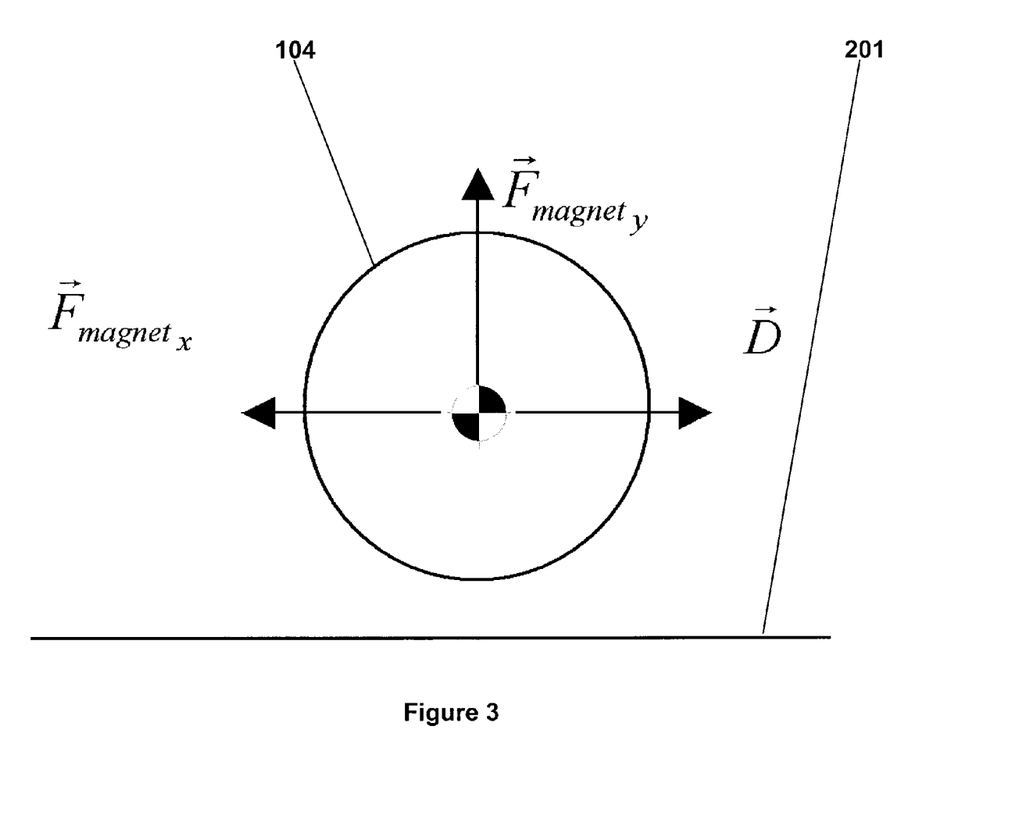
FIG. 3 is a schematic diagram showing magnetic and drag force vectors applied to the sphere of the illustrative embodiment of FIG. 1.

As the 18 mT/m magnetic field gradient applied during the tests was not strong enough to levitate the sphere 104, mechanical impulses were applied on the PMMA tube 103 in order to detach the sphere 104 from the bottom wall 201. Then, as shown in FIG. 3, the magnetic $\vec{F}_{magnet_x}$ and drag $\vec{D}$ force were directly opposed as shown in FIG. 3. FIG. 4 is a photograph of the set-up used during the tests.

The measurements were made as follows: the gradients were turned on while the valve of the flowmeter 107 was opened completely (maximum flow 105, sphere 104 on the net 106). Then, the valve of the flowmeter 107 was progressively closed until the sphere 104 started moving against the flow 105. And finally it was adjusted so that the sphere 104 finds equilibrium inside the tube 103. The measurements were repeated with a 6 mT/m horizontal gradient ($\vec{F}_{magnet_x}$) and 18 mT/m vertical gradient ($\vec{F}_{magnet_y}$). Both gradients had a cycle of 10 ms on and 2 ms off. The equilibrium flow is recorded in table 1. Table 1 shows that standard MRI systems can move a ferromagnetic sphere in a flow of liquid. In the tests reported in table 1, the diameter of the sphere 104 was half the diameter of the tube 103.

TABLE 1

| Magnetic field Gradient (mT/m) | Flow (l/min.) | Mean Velocity (m/s) |
|---|---|---|
| 18 | 0.4115 | 0.217 |
| 6 | 0.1775 | 0.093 |

Peripheral arteries have a diameter and flow of the same order of magnitude as the diameter and flow that were used in the set-up of FIG. 1 during the tests. The above results clearly show that it is possible to use MRI systems to move a ferromagnetic body in a flow inside a duct with a Reynolds number close to biological situations.

The tests were made using water instead of blood as a fluid. Blood's relative density is 1.05. As drag forces are proportional to the density of the fluid and as the blood has a Newtonian behavior in vessels having a diameter higher than 1 mm, [Milnor W. R. *Hemodynamics*, Baltimore/London: 1982], the drag forces should be 1.05 times stronger if the liquid is blood.

The shape of the immersed body is of primary concern. If it had been streamlined (ellipsoidal or drop shaped) and kept the same volume (same magnetic force), its drag would have been lower and it would have been able to withstand a higher flow since its drag coefficient would have been lowered [White F. M. *Fluid Mechanics* fourth edition, McGraw and Hill, 1999].

As described in [Wham, R. M., Basaran, O. A., and Byers, C. H., *Wall effects on flow past solid spheres at finite Reynolds number*, Industrial & Engineering Chemistry Research, Vol. 35, No. 3. March, pp. 864-874, 1996. 0888-5885. Oak Ridge Natl Lab, TN, USA] [Wham, R. M., Basaran, O. A., and Byers, C. H., *Wall effects on flow past fluid spheres at finite Reynolds number: Wake structure and drag correlations*, Chemical Engineering Science, Vol. 52, No. 19. October, pp. 3345-3367, 1997. 0009-2509. Oak Ridge Natl Lab, TN, USA] the drag is higher if the ratio between sphere diameter and tube diameter is higher. If the tests had been made with a smaller sphere compared to the tube, the maximum flow would have been comparatively higher.

Using a MRI system capable of producing stronger magnetic field gradients could optimize the magnetic force. For example, as the magnetic force is proportional to the gradient, a 40 mT/m system will provide 2.22 times more force while a 70 mT/m will provide 3.89 times more force.

Using a ferromagnetic material with a stronger saturation magnetization is another way to enhance the magnetic force. The balls (spheres) used in these tests were made of 1010/1020 carbon steel with a saturation induction $\vec{B}_{sat}$ of 1.67 T. It is reported in the literature that the CoFe (Permendur) alloys provide the highest saturation induction ($\vec{B}_{sat}$=2.45 T for Permendur) [Chen C-W. *Magnetism and Metallurgy of Soft Magnetic Materials*, Amsterdam New York Oxford: North-Holland, 1977] [Lacroux G. *Les Aimants Permanents*, Paris: Technique et Documentation, 1989]. A ⅛" permendur sphere with 70 mT/m gradients will provide 5.71 times more magnetic force.

Also, a field of force other than a magnetic field could potentially be used.

Tracking of the Microrobot

As indicated in the foregoing description, Magnetic Resonance Imaging (MRI) systems present the advantage that, while they are used to produce, in a controllable manner, the required three-dimensional magnetic field gradient, their imaging capabilities can be used to track the displacement of the microrobot in the blood vessel, thereby providing position feedback information.

To compensate for the artefacts produced by the presence of a body of ferromagnetic material during image generation, the software of the MRI system could be modified to introduce a mathematical model of the microrobot's magnetization. The modified MRI-based software would then compensate the effects of the body of ferromagnetic material on every step of the imaging process.

Another approach would be to develop an image-processing algorithm to track a known artefact in the distorted image from a mathematical model of this artefact or from an artefact database. Once the artefact is found, it would be linked to the robot's position.

Alternatively, any other types of tracking system could be used to determine the position and follow the progression of the displacement of the microrobot through the blood vessel.

Although the present invention has been described in the foregoing specification by means of an illustrative embodiment, this illustrative embodiment can be modified at will, within the scope of the appended claims, without departing from the spirit and nature of the subject invention.

What is claimed is:

1. An apparatus for tracking, propelling and controlling the displacement of an untethered body including magnetic field responsive material in a blood vessel of a subject, the apparatus comprising:

a magnetic resonance imager (MRI) including:

a bore magnet configured to produce an intense magnetic field sufficient to magnetically saturate the magnetic field responsive material of the body, said bore magnet having a hollow interior sized to receive the subject therein;

a multi-dimensional magnetic field generator configured to generate a variable magnetic field gradient having a direction and magnitude; and a tracking unit configured to acquire an MRI image of the position of the body in the blood vessel and to provide position feedback information;

a trajectory calculator configured to calculate a trajectory of the body in the blood vessel based at least upon the position feedback information of the body determined by the tracking unit of the MRI, a configuration of the blood vessel, and a target location to be reached by the body; and a gradient calculator configured to calculate the direction and magnitude of the gradient of the multi-dimensional magnetic field required to be applied to the magnetically-saturated body in order to propel and displace the body along the trajectory calculated by the trajectory calculator;

wherein a) the generator of the MRI is configured to apply the gradient calculated by the gradient calculator to the body, and b) both the generator and the tracking unit are part of the same MRI.

2. An apparatus as defined in claim 1, wherein the body includes a shell that comprises the magnetic field responsive material.

3. An apparatus as defined in claim 1, wherein the magnetic field responsive material is a ferromagnetic material.

4. An apparatus as defined in claim 1, wherein the gradient calculator is configured to calculate the direction and magnitude of the gradient of the multi-dimensional magnetic field using:

the equation $$\vec{\tau} = \vec{m} \times \vec{B} = V_{ferro} \vec{M} \times \vec{B}; \text{ and}$$

the equation $$\vec{F}_{magnetic} = V_{ferro} \vec{M} \cdot \nabla \vec{B},$$

wherein:

$\vec{\tau}$ =torque induced on the body;

$\vec{m}$=magnetic moment of the magnetic field responsive material;

$\vec{B}$=multi-dimensional magnetic field;

$V_{ferro}$=volume of the magnetic field responsive material;

$\vec{M}$=magnetization of the magnetic field responsive material;

$\vec{F}_{magnetic}$=force induced on the body;

$\nabla \vec{B}$=gradient of the multi-dimensional magnetic field.

5. A method for tracking, propelling and controlling the displacement of an untethered body including magnetic field responsive material in a blood vessel of a subject, the method comprising:

providing a MRI (Magnetic Resonance Imager) including:
a bore magnet configured to produce an intense magnetic field sufficient to magnetically saturate the magnetic field responsive material of the body, said bore magnet having a hollow interior sized to receive the subject therein;

a multi-dimensional magnetic field generator configured to generate a variable magnetic field gradient having a direction and an magnitude; and a tracking unit configured to acquire an MRI image of a position of the body in the blood vessel;

using the tracking unit of the MRI to determine the position of the body in the blood vessel while the body is magnetically-saturated and to provide position feedback information;

calculating a trajectory of the body in the blood vessel based at least upon the position feedback information of the body in the blood vessel, a configuration of the blood vessel, and a target location to be reached by the body;

calculating the direction and magnitude of the gradient of the multi-dimensional magnetic field required to be applied to the body, while the body is magnetically-saturated, in order to propel and displace the magnetically-saturated body along the calculated trajectory; and using the generator of the MRI to generate a multi-dimensional magnetic field based upon the calculated gradient and to apply it to the magnetically-saturated body, thereby propelling and displacing the magnetically-saturated body along the calculated trajectory.

6. A method as defined in claim 5, wherein a shell of the body comprises the magnetic field responsive material.

7. A method as defined in claim 5, wherein the body comprises a ferromagnetic material.

8. A method as defined in claim 5, wherein calculating the direction and magnitude of the gradient of the multi-dimensional magnetic field comprises:

using the equation $$\vec{\tau} = \vec{m} \times \vec{B} = V_{ferro} \vec{M} \times \vec{B}; \text{ and}$$

using the equation $$\vec{F}_{magnetic} = V_{ferro} \vec{M} \cdot \nabla \vec{B},$$

wherein:

$\vec{\tau}$ =torque induced on the body;

$\vec{m}$=magnetic moment of the magnetic field responsive material;

$\vec{B}$=multi-dimensional magnetic field;

$V_{ferro}$=volume of the magnetic field responsive material;

$\vec{M}$=magnetization of the magnetic field responsive material;

$\vec{F}_{magnetic}$=force induced on the body;

$\nabla \vec{B}$=gradient of the multi-dimensional magnetic field.

9. A magnetic resonance imager (MRI) configured to propel at least one magnetic field responsive body within a subject, comprising:

a bore magnet configured to produce an intense magnetic field sufficient to magnetically saturate the magnetic field responsive body, said bore magnet having a hollow interior sized to receive the subject therein;

a magnetic field gradient generator configured to generate and apply variable magnetic field gradients to at least a portion of the subject surrounding the body while the body is being magnetically-saturated by the bore magnet;

a controller configured to:
control the magnetic field gradient generator to acquire image data of the magnetically-saturated body within the subject using magnetic field gradients applied by the magnetic field gradient generator and instruct the magnetic field gradient generator to apply a calculated magnetic gradient that will propel the magnetically-saturated body towards a target location in the subject; and a tracking unit configured to provide position feedback information of the magnetically-saturated body using the acquired image data.

10. The MRI system as defined in claim 9, wherein at least one of the tracking unit and the controller is further configured to compensate for artifacts produced by the magnetically-saturated body in an image generated by the tracking unit.

11. The MRI system as defined in claim 10, wherein at least one of the tracking unit and the controller further comprises:
  a trajectory calculator configured to calculate a trajectory of the magnetically-saturated body based upon at least the position feedback information of the magnetically-saturated body, the configuration of body tissue surrounding the magnetically-saturated body and the target location; and
  a gradient calculator configured to calculate a direction and magnitude of the magnetic field gradient required to be applied to the magnetically-saturated body in order to propel the magnetically-saturated body along the trajectory calculated by the trajectory calculator.

12. The MRI system as defined in claim 10, wherein the magnetic field responsive body comprises ferromagnetic material and the tracking unit is configured to utilize a mathematical model of the magnetization of the magnetic field responsive body to compensate the effects of the ferromagnetic material on the image generated by the tracking unit.

13. The MRI system as defined in claim 10, wherein the tracking unit is configured to use an image processing algorithm to track a known artifact using a mathematical model of the artifact, wherein the position of the magnetic field responsive body is obtained from a determined position of the artifact.

14. The MRI system as defined in claim 9, wherein the calculated magnetic gradient is at least 6 mT/m.

15. A method for moving a body, which comprises magnetic field responsive material, inside a subject in order to reach a predetermined location within the subject, the method comprising:
  (i) applying an intense, static magnetic field at least to the body located inside the subject using a magnet of a magnetic resonance imager, wherein the intense, static magnetic field magnetically saturates the magnetic field responsive material of the body,
  (ii) applying a sequence of imaging magnetic field gradients to at least the magnetically-saturated body, the sequence of imaging magnetic field gradients being generated by a magnetic field gradient generator of the magnetic resonance imager,
  (iii) determining position feedback information of the magnetically-saturated body inside the subject using a tracking unit of the magnetic resonance imager and the applied sequence of imaging magnetic field gradients,
  (iv) applying a magnetic field gradient sufficient to propel the magnetically-saturated body in a desired direction towards the predetermined location, the propulsion magnetic field gradient being generated by the magnetic field gradient generator of the magnetic resonance imager, and
  (v) repeating steps (ii)-(iv) until the body has reached the predetermined location inside the subject.

16. The method as defined in claim 15, further comprising:
  calculating a trajectory of the body based at least upon the position feedback information of the magnetically-saturated body, the configuration of body tissue surrounding of the body and the predetermined location to be reached by the body and
  calculating the magnetic field gradient, which will propel the magnetically-saturated body in the desired direction within the subject, using the calculated trajectory.

17. The method as defined in claim 15, further comprising:
  generating an image of body tissue surrounding the magnetically-saturated body using the tracking unit and
  compensating for artifacts produced by the magnetic field responsive material in the image.

18. The method as defined in claim 15, wherein the magnetic field gradient applied in step (iv) is constant throughout each step (iv) and is recalculated after each repeated step (iii).

19. A microrobot system, comprising:
  a microrobot configured to be displaced within a patient, the microrobot comprising a magnetic field responsive material;
  a magnet configured to produce a static magnetic field sufficient to fully magnetize the magnetic field responsive material of the microrobot;
  a magnetic field gradient generator configured to generate and apply variable magnetic field gradients to the microrobot; and
  a controller configured to instruct the magnetic field gradient generator to apply:
    (i) a sequence of magnetic field gradients for acquiring image data of the microrobot within the patient, while the magnetic field responsive material is fully-magnetized, and
    (ii) a calculated magnetic field gradient that will propel the microbot, while the magnetic field responsive material is fully-magnetized, towards a target location in the patient.

20. A microrobot system as defined in claim 19, wherein the controller is configured to calculate a direction and magnitude of the magnetic field gradient sufficient to controllably propel the microrobot within the patient.

21. A microrobot system as defined in claim 19, wherein at least a shell of the microrobot is formed of the magnetic field responsive material.

22. A microrobot system as defined in claim 19, wherein the magnetic field responsive material is selected from steel and CoFe.

23. A microrobot system as defined in claim 19, further comprising an image generator configured to:
  track a position of the microrobot within the patient using varying magnetic field gradients applied by the magnetic field gradient generator.

24. A microrobot system as defined in claim 23, wherein the image generator is further configured to:
  compensate for artifacts produced by the magnetic field responsive material in an image of body tissue surrounding the microrobot.

25. A microrobot system as defined in claim 24, wherein at least a shell of the microrobot is formed of one of steel and CoFe and the controller is configured to calculate a direction and magnitude of the magnetic field gradient sufficient to controllably propel the microrobot within the patient.

26. A microbot system as defined in claim 19, wherein the calculated magnetic field gradient is at least 6 mT/m.

* * * * *